United States Patent
van Nifterick et al.

(10) Patent No.: US 6,287,119 B1
(45) Date of Patent: *Sep. 11, 2001

(54) METHOD OF MANUFACTURING A PROSTHESIS TO BE FIXED TO IMPLANTS IN THE JAWBONE OF A PATIENT, AND A SYSTEM FOR MANUFACTURING SUCH PROSTHESES

(75) Inventors: Willem Frederick van Nifterick; Johannis Adriaan Quaak, both of Amsterdam (NL)

(73) Assignee: Nobel Biocare AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/191,788

(22) Filed: Nov. 13, 1998

Related U.S. Application Data

(63) Continuation of application No. 08/583,005, filed on Jan. 26, 1996, now Pat. No. 5,857,853.

(30) Foreign Application Priority Data

| Jul. 26, 1993 | (NL) | ................................................. | 9301308 |
| Jul. 25, 1994 | (WO) | .................................. | PCT/NL94/00173 |

(51) Int. Cl.$^7$ .................................................. A61C 13/00
(52) U.S. Cl. .............................. 433/213; 433/68; 433/223
(58) Field of Search ............................... 433/29, 68, 172, 433/173, 174, 201.1, 213, 214, 223

(56) References Cited

U.S. PATENT DOCUMENTS

| 3,861,044 | 1/1975 | Swinson, Jr. | 433/213 |
| 4,324,546 | 4/1982 | Heitlinger et al. | 433/213 |
| 4,575,805 | 3/1986 | Moermann et al. | 433/68 |

(List continued on next page.)

FOREIGN PATENT DOCUMENTS

| 2 936 847 | 3/1981 | (DE) . |
| 33 20 395 | 12/1984 | (DE) . |
| 35 41 891 | 6/1987 | (DE) . |
| 282 615 | 9/1990 | (DE) . |
| 40 34 007 | 4/1992 | (DE) . |
| 0 025 911 | 4/1981 | (EP) . |
| 0 040 165 | 11/1981 | (EP) . |
| 0 091 876 | 10/1983 | (EP) . |

(List continued on next page.)

OTHER PUBLICATIONS

V. Stachniss and R. Stoll, "Computer Technologies in Dentistry Computerized Restorations: CEREC$^R$ and Other Methods," prepared for an International Symposium on Computer Restorations (May 3–4, 1991) entitled State of the Art of the CEREC–Method, at p. 33

Strid K.G. "On the application of photogrammetry to the fitting of jawbone–anchored bridges," *Prosthetic reconstructions on osseointegrated implants: Proceedings of the Gothenburg Conference*, (Sep. 1983), Alberktsson, T., et al. eds., *Swedish Dental Journal* (Stockholm 1985), at 93–105.

*Primary Examiner*—Ralph A. Lewis
(74) *Attorney, Agent, or Firm*—Fish & Neave; Jeffrey H. Ingerman

(57) ABSTRACT

The invention provides a method for manufacturing a prosthesis to be fixed to a plurality of implants in the jawbone of a patient. The method has as a characteristic feature that by means of at least one camera arranged at the opened mouth of the patient; images of the implants already fixed to the jaw of the patient are recorded from at least two different positions; these images are converted into electrical signals by at least one camera; by means of a photogrammetric method the electrical signals are processed using at least one calculating unit for obtaining positions and orientation information of the implants; and the positions and orientation information is used for the highly accurate manufacture of at least a part of the prosthesis.

22 Claims, 4 Drawing Sheets

U.S. PATENT DOCUMENTS

| | | | |
|---|---|---|---|
| 4,611,288 | 9/1986 | Duret et al. | 433/213 |
| 4,663,720 | 5/1987 | Duret et al. | 364/474 |
| 4,837,732 | 6/1989 | Brandestini et al. | 433/223 |
| 4,964,770 | 10/1990 | Steinbischler et al. | 433/223 |
| 5,052,928 | 10/1991 | Andersson | 433/172 |
| 5,154,612 | 10/1992 | Carlsson et al. | 433/173 |
| 5,224,049 | 6/1993 | Mushabac | 433/223 |
| 5,273,429 | 12/1993 | Rekow et al. | 433/223 |
| 5,320,462 | 6/1994 | Johansson et al. | 409/84 |
| 5,342,201 | 8/1994 | Oden | 433/223 |
| 5,401,170 | 3/1995 | Nonomura | 433/173 |
| 5,857,853 * | 1/1999 | van Nifterick et al. | 433/213 |

FOREIGN PATENT DOCUMENTS

| | | |
|---|---|---|
| 0 250 993 | 1/1988 | (EP) . |
| 0 299 490 | 1/1989 | (EP) . |
| 0 498 923 B1 | 8/1992 | (EP) . |
| 2 635 965 | 3/1990 | (FR) . |
| 2 682 473 | 4/1993 | (FR) . |
| 2 690 836 | 11/1993 | (FR) . |
| WO90/14803 | 12/1990 | (WO) . |
| WO91/03980 | 4/1991 | (WO) . |
| WO91/05520 | 5/1991 | (WO) . |
| WO91/18356 | 11/1991 | (WO) . |
| WO94/00074 | 1/1994 | (WO) . |

* cited by examiner

METHOD OF MANUFACTURING A PROSTHESIS TO BE FIXED TO IMPLANTS IN THE JAWBONE OF A PATIENT, AND A SYSTEM FOR MANUFACTURING SUCH PROSTHESES

This is a continuation of application Ser. No. 08/583,005 filed Jan. 26, 1996 now U.S. Pat. No. 5,857,853.

BACKGROUND OF THE INVENTION

The invention relates to a method of manufacturing a prosthesis to be fixed to implants in the jawbone of a patient.

More particularly, the invention relates to a method for enabling stress-free fixation of such prosthesis to implants.

The invention further relates to a system for manufacturing such prostheses. It is known in dentistry to fix prostheses onto implants; these are of cylindrical or helical shape and mostly made from a indifferent metal such as titanium or titanium compounds, and are preferably fitted in the toothless jaw. An implant has an internal screw thread by means of which the superstructure (bridge or prosthesis) is subsequently affixed with interposition of an insert (an intermediate ring).

After these dental implants have been placed in the jaw, an impression should be made for the finish and build-up of the prosthesis to be fitted. According to a conventional method, this impression is subsequently cast in plaster and with the aid of attachments a wax model is made. With this wax model, casting takes place in noble metal. The crown or bridge is then fitted in the mouth and placed.

Numerous drawbacks are inherent in this method. For instance the many steps in the process give rise to inaccuracies in the dimensioning. This leads to stresses in the prosthesis during fixation, which gives rise to undesired forces acting on the implants. The impossibility of making a construction which is completely free of stress used to be less of a drawback in the application to natural elements, since a natural tooth or molar is able to adjust to the situation to a certain extent because it is connected to the jawbone through a root membrane which allows some play. In the case of implants, by contrast, a rigid point (ankylosis) is involved. There has been much improvement in implantology over the last decade. However, the fabrication of stress-free superstructures remains one of the major problems. No really effective solution to this problem has been found to date.

In patients with implants, the stresses are transmitted through the implants to the surrounding jawbone. This can lead to microfractures and loss of the implant.

A crosspiece (which is in fact a rail between a number of implants) which has been screwed tight under tension also leads to substantial overloading and this may even lead to the implant being dislodged. In this connection it cannot be excluded that this is accompanied by damage to the jawbone, with all the attendant problems for the patient.

Apart from the foregoing, the risk is larger particularly with complex superstructures, which often rest on five to eight implants. In addition, placing implants with the superstructures resting thereon is a very costly affair.

Now, in the situation where in a patient a structure is used which rests on two or more implants, it is very important that the implantologist can be assured of complete success. If, for instance, in such a situation an implant comes loose, with all the attendant bone damage, the entire construction might be lost.

By means of X-ray photographs taken beforehand, the implantologist can determine the most suitable position for providing the cylindrical mortise holes for receiving the intraosteal implants, but because the arch of the jaw is not equally thick throughout, the possibility cannot be ruled out that upon subsequent placement of the prosthesis the implants introduced are not located equally high and do not run parallel. This can also be a source of stresses.

The article "State of the Art of the CEREC-Method" gives a summary of the systems known in 1991, in which a recording of a mouth or an impression of the mouth is digitized and fed to a computer, whereafter the computer controls a tool for making a prosthesis. It is clearly indicated at page 37 that photogrammetry is one of the possibilities of obtaining a three-dimensional image. For this purpose, for instance two cameras are used. One possible application is to make an image of a prepared tooth or molar, for the purpose of making a crown. Further, at page 41, section 3.1, the manufacturing of a frame is mentioned. At page 42, paragraph 3.4, the manufacture of an inlay and veneer is mentioned; and at page 44, sections 3.5 and 3.6 the manufacture of crowns and bridges is mentioned. At page 46 section 4, however, it is clearly stated that designing a prosthesis by means of a CAD/CAM system is still a fiction. It is not known, however, to make such images of implants for the purpose of making a prosthesis which is to be fixed to these implants. The present invention, however, surprisingly does allow the fabrication of a prosthesis which is to be fixed to implants. This is a definitive invalidation of the assumption generally accepted heretofore, that it is not properly possible to make prostheses by means of such a method. The invention provides the insight that this is quite possible, precisely for implants.

International patent application WO-90/14803 describes a method in which a three-dimensional recording is made and printed using photogrammetry. However, no recording is made in the patient's mouth. Instead, a model of the jaw of the patient is placed on a reference tray. Photographs are taken from different positions to enable the photographs to be processed in combination to obtain a 3D picture. The use of photogrammetry for the purpose of implants is not mentioned.

European patent application 0,040,165 describes in very general terms a process in which a 3D recording of a treated tooth is made. This recording is digitized and fed to a computer. The computer then controls a milling machine for manufacturing a crown. European patent application 0,054,785 describes in very general terms a comparable process as described above. Accordingly, it does not involve any prosthesis which is to be fixed to an implant.

European patent application 0,025,911 describes a process in which a copy of an object can be produced on the basis of a 3D recording of the object. The object in question can be a tooth but also a hand-made prosthesis. The recording is made using photogrammetry. All this means that no prosthesis fabricated by the use a CAD/CAM system is involved, where a 3D recording is made of a prepared tooth or molar to which this prosthesis will be fixed.

European patent application 0,250,993 relates to the making of recordings by means of a video camera. On the basis of a predetermined algorithm, the video image is frozen at a particular moment. On the basis of the still picture thus obtained, a further analysis is performed.

German patent application 33 20 395 describes a recording device which is placed over a tooth or a treated tooth for obtaining a 3D recording. If desired, the two recordings are compared and processed in combination by a computer for the purpose of fabricating a prosthesis.

German patent 282,615 of former East-Germany describes in very general terms a method for fabricating crowns on the basis of a 3D recording by means of a computer-controlled tool. However, this method involves the making of a replica of an object to be copied, on the basis of a 3D recording of that object.

In summary, it can be stated that the use of photogrammetry in a method for fixing dental prostheses onto implants in the jawbone of a patient is not known from any of the above-discussed publications.

Also known are methods and systems in which the object to be record is actively irradiated with electromagnetic waves.

Such methods and systems utilize, for instance, laser beams which are directed to the object under examination and the reflections of which are subsequently analyzed. According to another active method, a predetermined pattern, for instance a rectangular grating, is projected on the object in question. The pattern will be distorted depending in the shape of the object. Then an image of the object in digitized form is fed to a computer. By comparing the distorted pattern with the original pattern, an idea of the three-dimensional shape of the object can be obtained.

The following references relate to such active systems: FR 2,635,965; FR-2,682,473; FR-2,690,836; WO-91/03980; WO-91/18356; WO-91/05520; WO-94/00074; EP-0,299,490; EP-0,091,876; DE-4,034,007; DE-3,541,891 and U.S. Pat. No. 4,663,720.

The system according to the present invention, however, does not necessarily utilize active electromagnetic radiation sources that are part of the system.

SUMMARY OF THE INVENTION

Accordingly, the object of the invention is to provide a solution to the problems outlined and to develop a method to arrive at the fabrication of stress-free constructions and is characterized in that
  by means of at least one camera arranged at the opened mouth of the patient, from at least two different positions recording are made of the implants already fixed to the jaw of the patient;
  these recordings are converted into electrical signals;
  by means of a photogrammetric method the electrical signals are processed utilizing at least one calculating unit for obtaining position and orientation information of the implants;
  this position and orientation information is used for manufacturing at least a part of the prosthesis.

Because at least two recordings are made, in known manner a three-dimensional picture can be composed by the calculating unit. This picture can then be processed by the calculating unit in known manner for the purpose of obtaining highly accurate information about the position and orientation of the implants. If this information is used for the purpose of fabricating the prosthesis, a prosthesis is obtained which is adjusted to the position and orientation of the implants with a unprecedentedly high accuracy. This prosthesis can be fixed to the implants entirely free of stress. Because the implants have a reflective surface and moreover have predetermined dimensions, photogrammetric methods for making a prosthesis to be fixed to implants can be used advantageously in accordance with the invention.

According to a particular aspect of the invention, the relative position and orientation information is determined, respectively, from the position and orientation of the implants relative to each other. More particularly, the position and orientation information is converted by the calculating unit into control signals by which a tool can be controlled for carrying out mechanical operations on a material piece for the fabrication of at least a part of the prosthesis, in accurate correspondence with the position and orientation information.

The implants preferably comprise predetermined dimensions, information about these dimensions being processed in combination with the above-mentioned position and orientation information for obtaining position and orientation information as mentioned. More particularly, the implants comprise predetermined dimensions, information about these dimensions being processed in combination with the above-mentioned position and orientation information for determining material portions which are to be removed from the material piece by the tool for the purpose of fabricating at least the part of the prosthesis that is fixed to the implants.

According to a preferred embodiment of this method according to the invention, for that purpose in a method for fixing dental prostheses to implants in the jawbone, the procedure is such that orientation and position (positions) of the implants are converted by a number of cameras arranged around the opened mouth into an equal number of corresponding series of electronic signals, which, fixed as a recording track, can serve for the control of a turning and milling machine for carrying out mechanical operations on a metal prosthesis part, in accurate correspondence with those positions.

A system for fabricating a prosthesis to be fixed to implants in the jawbone of a patient is characterized in that the system comprises:
  at least one camera arranged at the opened mouth of the patient for making recordings of the implants already fixed to the jaw of the patient from at least two different positions;
  means for converting these recordings into electrical signals;
  a calculating unit which processes the electrical signals by means of a photogrammetric method for obtaining position and orientation information of the implants;
  a tool which fabricates at least a part of the prosthesis on the basis of the above-mentioned position and orientation information.

BRIEF DESCRIPTION OF THE DRAWINGS

The invention will be further elucidated with reference to the accompanying drawings.

FIG. 2a shows a side elevation of an insert to be screwed into an implant, which

DETAILED DESCRIPTION OF THE INVENTION

Figure 1:
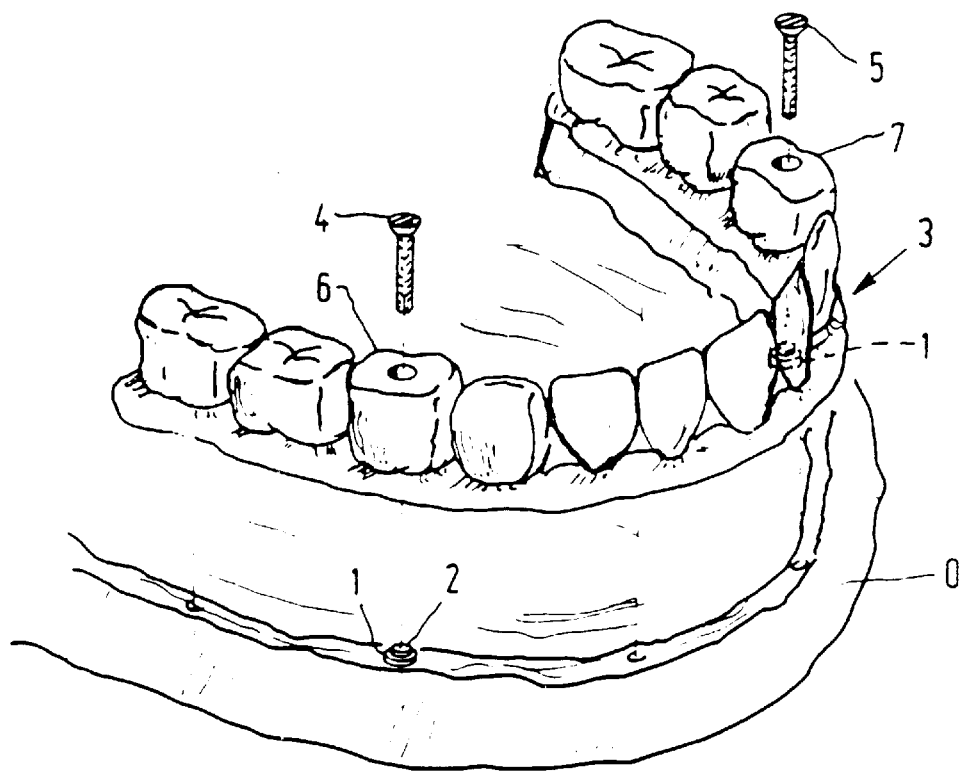
FIG. 1 shows in diagrammatic perspective an arch of a human jaw without teeth, which includes a few already placed implants with inserts, as well as an extensive prosthesis, which can be fixed by means of a few screws.

FIG. 1 diagrammatically shows a human lower jaw 0, which includes a number of implants (for instance six) place by an implantologist. To avoid crowding of the drawing, only two implants are indicated by the reference numeral 1. Inserts 2 have already been screwed to the implants for the purpose of subsequently carrying the superstructure 3. This superstructure 3 was heretofore fabricated by the conventional method mentioned, which method has all kinds of sources of possible stresses between the implants, as has been explained in the foregoing. The superstructure 3, which, in the example shown, comprises four incisors, two canines and two sets of three molars, is anchored in the mouth, in this example by means of small screws 4, 5 which are screwed into the inserts 2. In the situation depicted, these screws 4, 5 extend through molars 6, 7 on the superstructure 3, but the superstructure can also be affixed to the jaw next to the upper structure. After being screwed tight, the elements in question (6, 7) are filled.

Figure 2A:
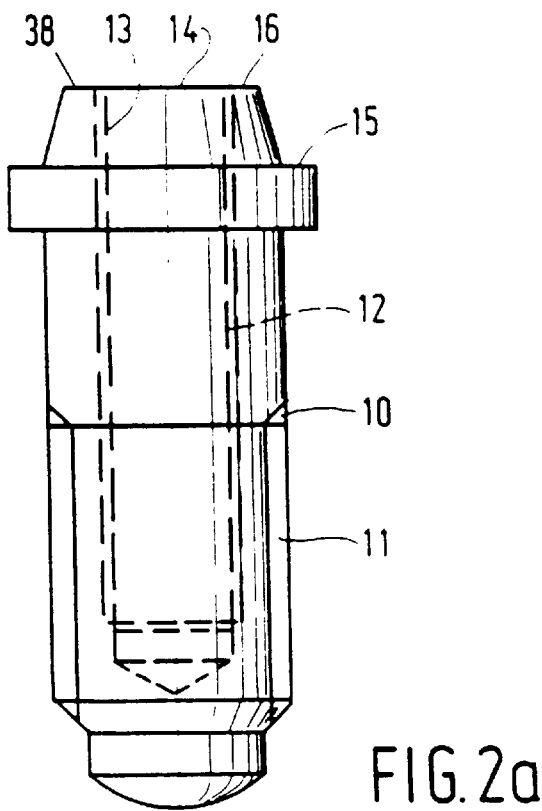

FIG. 2a shows, in side elevation and on a highly enlarged scale, a possible embodiment to fan insert 10 to be screwed into an implant. Both the implant and the insert normally consist of metal such as titanium.

To screw the insert to the implant, the implant carries an external thread 11 on the cylindrical outside at the lower end. The insert 10 is provided, at the top thereof, with a longitudinal bore 12 having therein an internal thread 13 for receiving the fastening screws (4, 5; FIG. 1). In this exemplary embodiment, the insert 10 comprises, at the top around the opening 14 or the bore 12, a stepped form with two concentric rings 15 and 16 at two levels separated in the longitudinal direction of the insert 10.

Figure 2B:
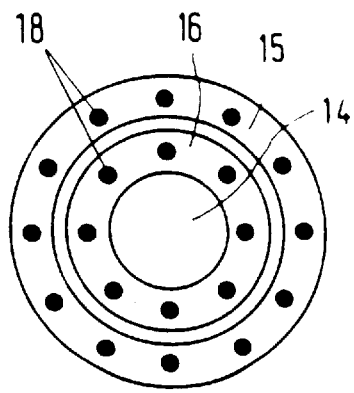
FIG. 2b shows the top side of this insert.

It can be seen in FIG. 2b that the two concentric rings 15 and 16 on the top of the insert are each provided with an accurately provided concentric recognition pattern of optical recognition points 18.

These recognition points 18, for instance engraved by means of a laser beam, may be provided for the benefit of the photogrammetric recordings and are then preferably of miniscule design, for instance 100 to 150 microns in diameter. Because the heads of the inserts projecting above the implants tend to glow upon exposure for the purpose of the photogrammetric recordings, the engraved recognition points have been colored white for a better contrast.

It has even been found possible, in accordance with a particular aspect of the invention, to omit these recognition points, which, of course, imposes stringent requirements on the camera.

Figure 3:
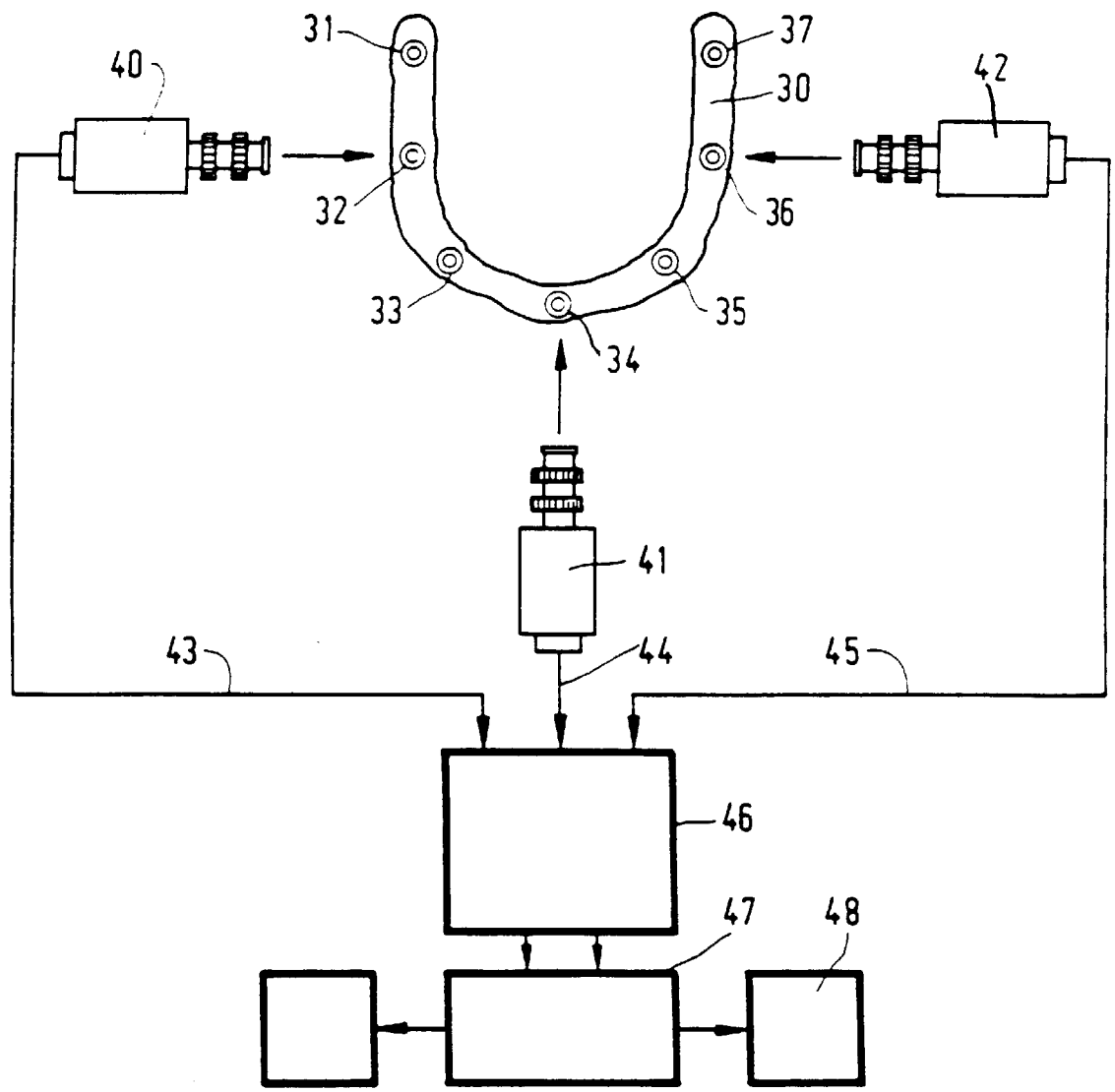
FIG. 3 schematically shows an arch of a jaw having placed therein a few implants with inserts, which are photographed by means of a number of cameras arranged around the jaw, as well as the interface and the calculating unit and the equipment for fixing the recording functions.

FIG. 3 shows a diagrammatic top plan view of the arch of a jaw 30 in which seven inserts 31–37 have been fitted in the implants (not shown in the drawing). These inserts 31–37 will generally have their top surfaces disposed at different levels, while further the longitudinal axes of the implants, and hence the longitudinal axes of inserts screwed into them, will almost never run parallel.

As FIG. 3 shows, a number of cameras 40, 41, 42 have been arranged around the arch 30, all disposed in the same plane, approximately in the plane of the arch 30. They are special cameras, such as for instance pixel cameras or ccd cameras, in which the image obtained with an optical lens is projected on a screen and is converted into a series of electronic signals through electronic scanning procedures.

The number of cameras shown in FIG. 3 is three, which is adequate to obtain a good survey of the different inserts. From a theoretical point of view, however, two cameras are sufficient. On the other hand, it has also been found to be possible to use a single camera, which is then swivelled around the mouth at short intervals into at least two accurately defined positions and makes the pictures in succession.

Each camera is in communication with an interface 46 through a corresponding connecting cable 43, 44, 45, which interface 46 can provide for the conversion of the signals into digital form. It is also possible, however, to utilize a very modern camera, in which the recorded images appear at the output terminals directly in digital form. The interface 46 is connected to a powerful calculating unit 47, which provides an analysis of the received signals in that the received electronic signals are processed and combined in coordinates of the different inserts, and their axes and their top surfaces, and the calculating unit 47 transmits these data, again in digitized form, as recording functions to a recording device 48, in order to be recorded there on a suitable recording medium such as a magnetic tape or possibly a diskette. The calculating unit is provided with software which is known per se, for determining coordinates defining the position and orientation of the implants and/or inserts. In particular, the relative orientation and position are determined, i.e., the orientation and position of the implants relative to each other. Because the implants and/or inserts have predetermined dimensions, the calculating unit can process the information about these dimensions in combination with the above-mentioned position and orientation information for obtaining the information for determining the dimensions of a prosthesis which can be fixed to the implants free of stress. If the dimensions of the implants and/or the inserts are not known, these too can be determined, in accordance with the invention, by photogrammetric route, but this will generally yield less accurate results than the preferred embodiment outlined above. If the dimensions of the implants and/or the inserts are predetermined, this information can also be used in known manner to recognize the inserts and/or implants by the photogrammetric method (pattern recognition which makes it possible to accurately determine the above-mentioned position and orientation information.

Preferably, recordings of implants are taken when they comprise inserts. Preferably, the inserts are cylindrical, while the calculating unit determines ellipse variables of the circumferential edge of an insert and determines the position orientation information on the basis of these variables. These variables can, for instance, be the variables of dimension flattening, and angle.

If an object provided with a number of calibrated optical recognition points is introduced into a patient's mouth, these points can function as reference. As described hereinbefore, a number of implants are provided with at least one optical recognition point. This is understood to include inserts which are connected to the implants and are provided with optical recognition points. These recognition points are used for the photogrammetric determination of the orientation and position. In particular, for the purpose of the photogrammetric determination of the course of the longitudinal axes of the inserts, these are provided with calibrated optical recognition points at their top surface. In addition, a recognition means can be attached to an implant or inserts, the recognition means being provided with calibrated optical recognition points. As will be discussed hereinafter, these optical recognition points have, for instance, a predetermined position relative to the implant and/or insert when the recognition means is attached to it. As a consequence, on the basis of the photogrammetric determination of the position of the recognition points, the orientation and position of the associated implant and/or insert can be determined.

The above-mentioned magnetic recording medium, after the data associated with the patient in question have been record, is taken out of the device 48 in order to be utilized in a different place and at a different time for controlling a five- or six-axis turning and milling machine for mechanically machining a metal part of the later prosthesis, for instance a crosspiece, on which the superstructure is subsequently fitted. The drive of the turning and milling machine takes place in accordance with the values of the above-mentioned coordinates as found by the photogrammetric route, which is known per se, in a manner so accurate that in the product the position and the orientation of the later fixing holes correspond with the recorded situation in the mouth to within a few microns.

In order that a fixed reference be available when recordings are being made, it is preferred, in the practice of the method according to the invention, to use a measuring scale shown in more detail in FIGS. 4a–4e.

Figure 4B:
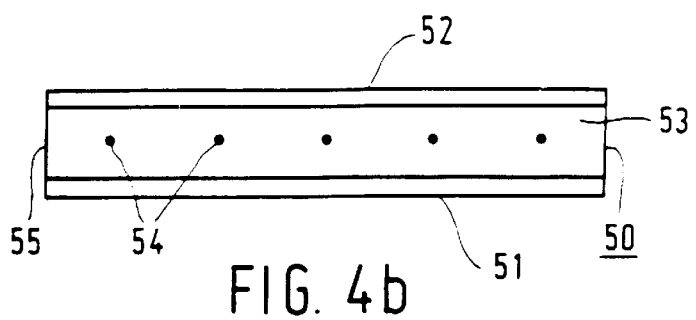
FIGS. 4a–4e show the measuring scale to be placed in one of the inserts or implants as a recognition means.
Figure 4A:
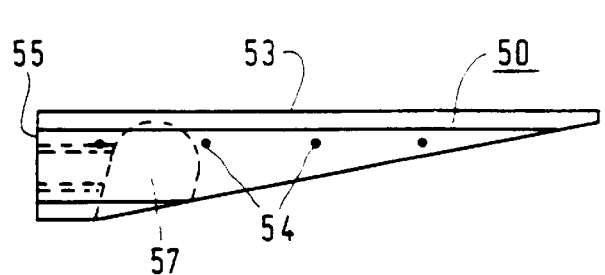
Figure 4C:
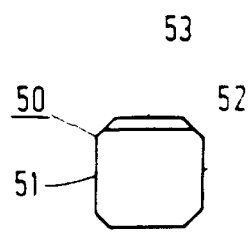
Figure 4D:
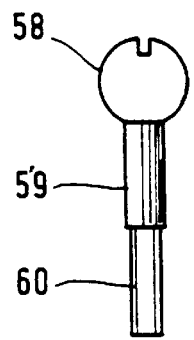
Figure 4E:
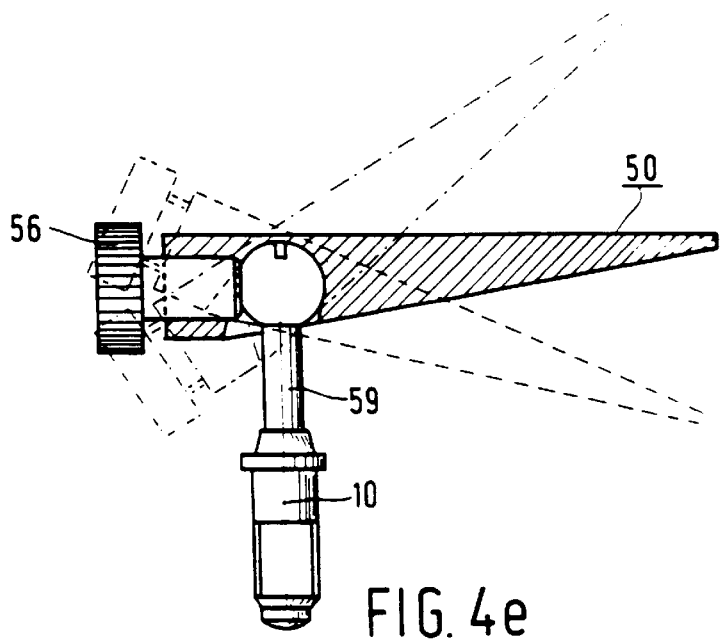

FIG. 4a shows a small bar 50 used for this purpose, showing a trapezoidal shape in side elevation;

FIG. 4b shows the top plan view of the bar 50;

FIG. 4c shows the right-hand end view of the bar;

FIG. 4d shows a pin 59 with a round head 58, to be screwed into an insert; and FIG. 4e shows the assembled measuring scale screwed on an insert 10.

This measuring scale, as a recognition or identification means during photogrammetric work, accordingly consists of a small bar 50, of substantially rectangular cross section, which bar, on three sides thereof, viz. the two sides 51, 52 and the top side 53, is provided with a row of optical marking points 54 of very minor dimensions, which marking points 54 have been engraved very accurately, for instance by means of a laser beam. The diameter of the marking points 54 is, for instance, 100 to 200 microns. The relative distances of these points 54 are calibrated. To increase the contrast, the bar 50 has, for instance, been colored dark blue and the marking points 54 have been colored white. The bar 50, at the blunt end 55 thereof is provided with internal thread, in which a screw knob 56 can be manually turned by the implantologist. At the underside the bar 50 comprises a spherical recess 57 for receiving therein a round head 58. This round head 58 forms the top end of a pin 59 provided, at the lower end thereof, with screw thread 60 for screwing the measuring scale into an insert 10 on the jaw of the patient (FIG. 4e).

To make recordings with the cameras, the assembled measuring scale according to FIG. 4a along with the insert 10 is screwed into one of the implants placed in the arch of the jaw. At this point it cannot be predicted whether the axis of the selected implant is vertical. However, in order that, in the case of a non-vertical axis, the bar 50 nevertheless extends level in the mouth as far as possible, the bar 50 is tilted about the round head 58 of the pin 59 screwed into the insert 10, until it has the desired level orientation and is then secured with the screw knob 56.

The recordings by the cameras derive their scale of reference from the calibrated distances of the measuring points 54.

Figure 5:
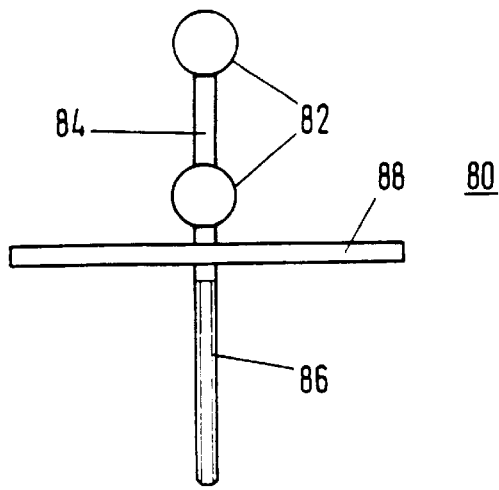
FIG. 5 shows a recognition means to be fixed to one of the inserts and/or implants.

FIG. 5 shows a recognition means 80 comprising at least two spheres 82 which have been fixedly positioned relative to each other and are mounted on a pin 84. At its lower end 86, the pin 84 is provided with screw thread and can thereby be secured to an implant and/or insert in the mouth of a patient. The white spheres 82 represent the actual measuring objects. They offer a good possibility of providing contrast and can be automatically located and measured. In this connection it is important that a spherical shape is imaged as a circle under any angle of view of a camera. This will facilitate the automatic measurement of the centres of the spheres as a representation of the insert axis. The inclined orientation of the insert and/or implant can be derived from the coordinates of the centre of the two spheres. For this purpose, it is important that the pin and the spheres accurately in line. If the distance between the centres of the two spheres is known as a fixed measure, this method at the same time provides an elegant solution for the provision of scale in the images. This can be realized by making the recognition means in one piece. In particular, the recognition means further comprises a plate 88 to indicate the proper height of the insert and to cancel any play in the screw thread. Optionally, the plate can be painted black and so serve as a contrastive background to the white spheres. Alternatively, an elastic black backdrop can be slid over the spheres. Also, the edge of this plate can be ribbed, so that the indicator can be easily screwed into the insert. In addition, from the centres of spheres associated different implants and/or inserts, the relative position and orientation of the corresponding implants and/or inserts with respect to each other can be determined.

Figure 6:
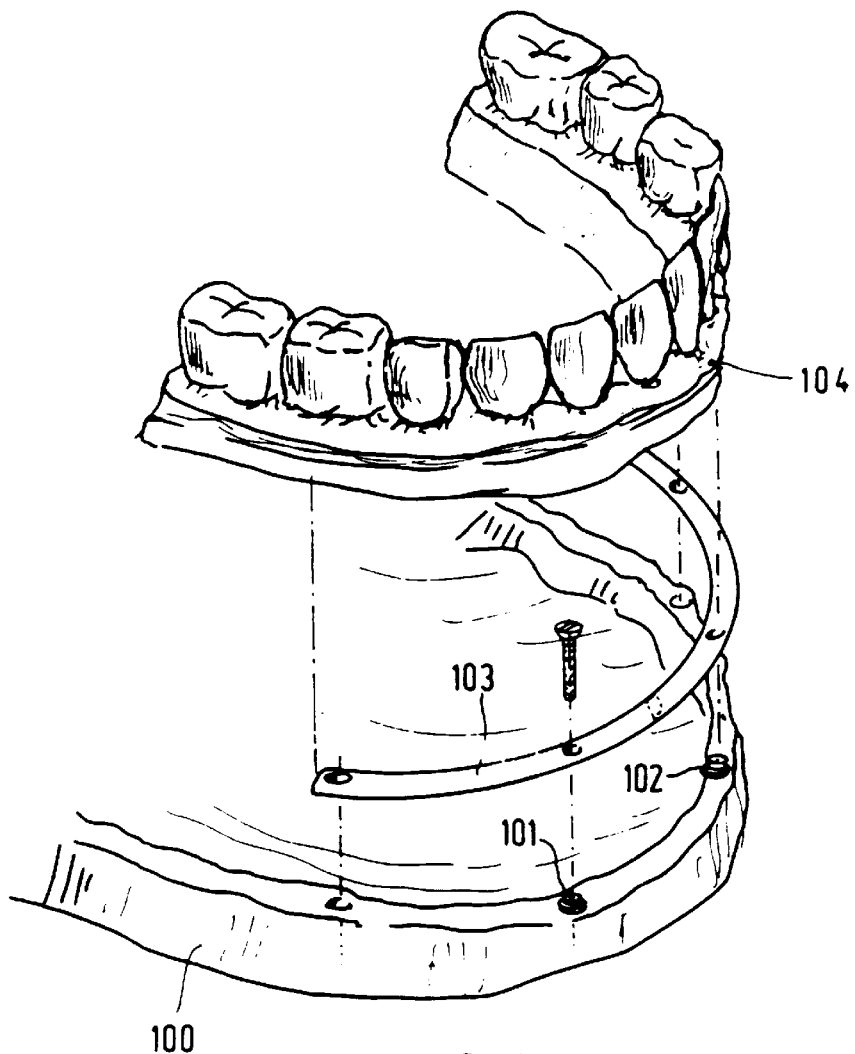
FIG. 6 shows a different principle of fixing a prosthesis on a jaw, where the invention can also be used.

The invention, in terms of its application, is not in any way limited to the manner of fixing a superstructure as discussed with reference to FIG. 1, but can equally successfully be applied to a covering prosthesis as shown in FIG. 6.

Here, for instance four implants have been placed in a patient's mandibular arch 100. Two implants are shown in the drawing in the front of the arch and indicated with reference numerals 101 and 102. The implants 101, 102 and possibly others are connected to each other with a crosspiece construction 103, which is bent in this example, for instance of substantially egg-shaped cross-section with the small end directed downwards, which comes to lie somewhat above on top of the wall of the jaw. In the example shown, this crosspiece 103 is fixed onto inserts in the implants, for instance by means of small screws. The crosspiece 103 and the holes provided therein are made using the above-described photogrammetric recording methods and the CAM methods and can later be secured on the implants 101, 102 in the arch 100 entirely without stress.

The actual prosthesis 104 is of the clip-on type and to that end comprises a metal base having at the underside thereof a concavity complementary to the contour of the crosspiece construction 103. Accordingly, this prosthesis 104 can be slipped around the crosspiece 103 onto the jaw 100 with a close fit.

Other forms of implants and prostheses, too, lend themselves for use of the invention.

While recording the coordinate data by means of the cameras arranged around the opened mouth of the patient, it is possible—for the purpose of increasing the accuracy of the measurement inasmuch as a better spatial impression is thereby provided—to move the entire arrangement parallel to itself in upward direction over a slight distance, say a few centimeters. Immediately thereafter, again recordings are made from this slightly higher position. By comparing the signals, the software governing the calculating unit can determine the coordinates of the positions of the different inserts and the measuring scale unequivocally and with great accuracy. The height and the orientation of the top surfaces of all of the inserts can be determined very accurately, which is indispensable in the fabrication of the prosthesis to provide for stress-free placement in the mouth.

The recorded data coming from the calculating unit are made available to a five- or six-axis turning and milling machine. By means thereof, a crosspiece or connecting plate can be made which subsequently forms a perfect close fit with the measured insert surfaces and is provided with throughbores perfectly in line with the axes of the implants and inserts as placed. By the use of this advanced technique, the three-dimensional coordinates are accurate to within 20–30 microns.

The photo cameras are basically achromatic electronic image recording tubes. To obtain the desired information with regard to the minuscule recognition points, a good depth of focus is essential, which imposes stringent optical requirements on the optics of the lens and the diaphragm. Because the recognition points on the inserts and on the measuring scale have been made white, a high brightness sensitivity of the target inside of the camera, on which the light impressions are collected via the optical lens, is essential. Because these objects to be recorded basically do not move, the operation of the target may otherwise be fairly slow. The achromatic images recorded by the cameras is transmitted to the interface as a video signal containing the requested information, in order to be converted in the interface into the digital form which is fed to the calculating unit.

The photogrammetric equipment is, of course, arranged at the implantologist's. The data recorded on magnetic recording medium are used in the dental laboratory in the manner analogous to that known as computer aided manufacturing (CAM) for numerical control of the suitable production machine.

an important advantage of the invention is that it eliminates the occurrence of situations where superstructures have to be made again, implants have to be re-made because they do not fit or cause stresses in the arch of the jaw as well as the loss of implants with all the harmful health consequences thereof. The technique described can naturally be used as well for patients with superstructures on natural elements.

Accordingly, this entails the advantages that the dental laboratories can work more accurately and even in those situations can preclude internal errors. It then prevents products having to be re-made because of the laboratory's own mistakes. This development will lead to a saving on labor time and cost, also for the dentist. From a health service point of view, too, this aspect is not unimportant. In addition, the method according to the present invention can be qualified as more hygienic and patient-friendly in all respects.

A major advantage is also that stress-free superstructures clearly prolong the life of implants. Further, a well-nigh unlimited range of applications in the medical field is possible. In the development of dentistry this method is a major step forward.

What is claimed is:

1. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants; and manufacturing at least a part of the prosthesis using the implant positions and orientation information of the plurality of implants; and converting the implant positions and orientation information into control signals, said control signals being for use in said manufacturing step for controlling a tool for performing mechanical operations on a material piece in accurate correspondence with the positions and orientation information wherein the plurality of implants have predetermined physical dimensions; and said processing comprises processing said positions and orientation information in combination with the predetermined dimensions to determine a portion of the material piece for removal by the tool during said manufacturing step such that a remaining portion of said piece can be fixed to the plurality of implants.

2. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants; and manufacturing at least a part of the prosthesis using the implant positions and orientation information of the plurality of implants, wherein the plurality of implants have predetermined physical dimensions, and wherein said processing comprises processing said positions and orientation information in combination with said physical dimensions using a pattern recognition method.

3. A method for manufacturing a prosthesis to be fixed to a plurality of implants in a jawbone of a patient, said method comprising the steps of:

recording images of said plurality of implants and one or more inserts using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants; and manufacturing at least a part of the prosthesis using the implant positions and orientation information of the plurality of implants, and wherein the one or more inserts are substantially cylindrical and are characterized by ellipse variables of a circumferential edge, said processing comprising:

determining the ellipse variables; and calculating said positions and orientation information using the ellipse variables.

4. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants;

manufacturing at least a part of the prosthesis using the implant positions; and introducing into the mouth a recognition means having at least one calibrated optical recognition point, said point appearing in said images so that said electrical signals corresponding to said point function as a reference during said processing, wherein said introducing comprises fixing said recognition means to an implant, said recognition means having at least one optical recognition point, and wherein said introducing comprises introducing into the mouth the recognition means having an adjustable bar which (1) comprises on three sides thereof a row of calibrated optical recognition points and (2) has an underside.

5. The method of claim 4 wherein:

the recognition means further comprises a pin having a round head; and said method further comprises screwing said pin into the implant so that said round head is received in a corresponding cavity at the underside of the bar and is fixed in a suitable position using a screw knob extending in the longitudinal direction of the bar.

6. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants;

manufacturing at least a part of the prosthesis using the implant positions; and introducing into the mouth a recognition means having at least one calibrated optical recognition point, said point appearing in said images so that said electrical signals corresponding to said point function as a reference during said processing, wherein said introducing comprises fixing said recognition means to an implant, said recognition means having at least one optical recognition point, and wherein said introducing comprises introducing into the mouth the recognition means which comprises at least two spheres, each of the spheres having a center fixedly positioned relative to each other, said spheres functioning as optical recognition points.

7. The method of claim 6 wherein each of the plurality of implants has an axis, said method further comprising securing the recognition means to the implant so that the spheres lie on the axis.

8. The method of claim 7 wherein said processing comprises:

determining a position for each center of the at least two spheres using the calculating unit; and determining the positions and orientation information of the plurality of implants using the positions of the centers.

9. The method of claim 8 wherein:

said recognition means includes at least a first recognition means and a second recognition means, each of the recognition means comprising at least one sphere having a center; and wherein the processing comprises:

determining a position for each center using the calculating unit, determining a relative position of each center using the position of the centers, and determining a relative position of each relevant implant using the relative positions of the centers.

10. The method of claim 6 wherein the processing comprises determining the position of each center for use as the reference.

11. The method of claim 6 wherein the implant has a longitudinal axis and wherein the recognition means further comprises:

a pin having a longitudinal axis, the spheres being attached to the pin in such a manner that the centers of the spheres lie on the longitudinal axis of the pin, and a flat plate attached at a right angle to the longitudinal axis of the pin, said method further comprising:

fixing the pin to the implant so that the longitudinal axis of the implant extends in the direction of the longitudinal axis of the pin.

12. A system for manufacturing a prosthesis to be fixed to a plurality of implants in a jawbone of a patient, said system comprising:

at least one camera for being positioned at the opened mouth of the patient for recording images of the plurality of implants already fixed to the jawbone from at least two different positions, wherein each of the plurality of implants has predetermined physical dimensions, and wherein said at least one camera is also for converting said images into electrical signals;

a calculating unit for processing the electrical signals using a photogrammetric method for obtaining implant positions and orientation information and for determining relative position and orientation information from implant positions and orientation information, wherein the calculating unit processes the predetermined dimensions in combination with the position and orientation information to determine a portion to be removed from the material piece such that a remaining portion of the material piece can be fixed to the plurality of implants; and a tool for manufacturing at least a part of the prosthesis using said implant positions and orientation information.

13. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants, wherein said processing comprises determining relative positions and orientation information from the implant positions and orientation information;

manufacturing at least a part of the prosthesis using the implant positions and orientation information of the plurality of implants;

converting the relative positions and orientation information into control signals, said control signals being for use in said manufacturing for controlling a tool to perform mechanical operations on a material piece in accurate correspondence with the position and orientation information, wherein the plurality of implants have predetermined physical dimensions; and said processing comprises processing said relative positions and orientation information in combination with the predetermined dimensions to determine a portion of the material piece for removal by the tool during the manufacturing such that a remaining portion can be fixed to the plurality of implants.

14. A method for manufacturing a prosthesis to be fixed to a plurality of implants in a jawbone of a patient, said method comprising the steps of:

recording images of said plurality of implants and one or more inserts using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants; and manufacturing at least a part of the prosthesis using the implant positions and orientation information of the plurality of implants wherein said processing comprises determining relative positions and orientation information from the implant positions and orientation information, wherein the inserts are substantially cylindrical and are characterized by ellipse variables of a circumferential edge, said processing comprising:
    determining the ellipse variables; and
    calculating said relative positions and orientation information using the ellipse variables.

15. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants;

manufacturing at least a part of the prosthesis using the implant positions and orientation information of the plurality of implants; and providing at least one optical recognition point for use with said processing step wherein said providing comprises fixing said recognition means to an implant, said recognition means having at least one optical recognition point, wherein said fixing comprises fixing said recognition means comprising an adjustable bar which (1) comprises on three sides thereof a row of calibrated optical recognition points and (2) has an underside.

16. The method of claim 15 wherein:
the recognition means further comprises a pin having a round head;
said method further comprising screwing said pin into the implant so that said round head is received in a corresponding cavity at the underside of the bar and is fixed in a suitable position using a screw driver extending in the longitudinal direction of the bar.

17. A method for manufacturing a prosthesis to be fixed to a plurality of implants in a jawbone of a patient, said method comprising the steps of:

recording images of said plurality of implants using at least one camera positioned at the opened mouth of the patient in at least two different positions;

converting said images into electrical signals by means of the at least one camera;

processing the electrical signals with at least one calculating unit using a photogrammetric method to obtain implant positions and orientation information of the implants;

manufacturing at least a part of the prosthesis using the implant positions and orientation information of the plurality of implants; and providing at least one optical recognition point for use with said processing step wherein said providing comprises fixing said recognition means to an implant, said recognition means having at least one optical recognition point, wherein said fixing comprises fixing said recognition means comprising at least two spheres, each of the spheres having a center fixedly positioned relative to each other, said spheres functioning as optical recognition points.

18. The method of claim 17 wherein each of the plurality of implants has an axis, said method further comprising securing the recognition means to the at least one of said plurality of implants so that the spheres lie on the axis.

19. The method of claim 18 wherein said processing comprises:
determining the positions of the centers of the at least two spheres using the calculating unit; and
determining the orientation of the plurality of implants using the positions of the centers.

20. The method of claim 19 wherein:
said recognition means includes at least a first recognition means and a second recognition means, each of the recognition means comprising at least one sphere having a center; and wherein
the processing comprises:
    determining the position of each of the centers using the calculating unit, and
    determining a relative position of each relevant implant using the relative positions of the centers.

21. The method of claim 19 wherein the processing comprises determining the position of each center for use as the reference.

22. The method of claim 17 wherein:
the at least one of said plurality of implants has a longitudinal axis, and
the recognition means further comprises:
  a pin having a longitudinal axis,
    the spheres being attached to the pin in such a manner that the centers of the spheres lie on the longitudinal axis of the pin, and
    a flat plate attached at a right angle to the longitudinal axis of the pin, said method further comprising:
    fixing the pin to the at least one of said plurality of implants so that the longitudinal axis of the implant extends in the direction of the longitudinal axis of the pin.

\* \* \* \* \*

UNITED STATES PATENT AND TRADEMARK OFFICE
CERTIFICATE OF CORRECTION

PATENT NO. : 6,287,119 B1
DATED : September 11, 2001
INVENTOR(S) : Willem van Nifterick et al.

It is certified that error appears in the above-identified patent and that said Letters Patent is hereby corrected as shown below:

Title page,
References Cited, OTHER PUBLICATIONS, line 5, change "p.33" to -- p. 33. --;

Column 1,
Line 19, change "from a indifferent" to -- from an indifferent --;
Line 42, change "point" to -- joint --;

Column 2,
Line 11, change "recording of a mouth" to -- recording of the mouth --;
Line 12, change "instance" to -- instance, --;
Line 17, change "3.6" to -- 3.6, --;
Line 19, change "mentioned. At" to -- mentioned; at --;
Line 59, change "will" to -- is to --;

Column 3,
Line 14, change "record" to -- recorded --;
Line 28, change "FR 2,635,965" to -- FR-2,635,965 --;

Column 4,
Line 56, change "which" to -- while --;

Column 5,
Line 7, change "place" to -- placed --;
Line 27, change "of metal" to -- of a metal --;

Column 6,
Line 42, change "(pattern recognition" to -- (pattern recognition) --;
Line 48, change "position" to -- position and --;

Column 7,
Line 8, change "record," to -- recorded, --;
Line 44, change " thereof" to -- thereof, --;

UNITED STATES PATENT AND TRADEMARK OFFICE
CERTIFICATE OF CORRECTION

PATENT NO. : 6,287,119 B1
DATED : September 11, 2001
INVENTOR(S) : Willem van Nifterick et al.

It is certified that error appears in the above-identified patent and that said Letters Patent is hereby corrected as shown below:

<u>Column 8,</u>
Line 13, change "spheres" to -- spheres be --;
Line 26, change "associated" to -- associated with --;
Line 27, change "and" to -- and/or --;
Line 34, change "instance" to -- instance, --;
Line 40, change "cross-section" to -- cross section --;

<u>Column 9,</u>
Line 26, change "is" to -- are --;
Line 38, change "an" to -- An --;

<u>Column 14,</u>
Line 65, change "19" in bold to -- 17 -- in bold.

Signed and Sealed this

Second Day of April, 2002

*Attest:*

*Attesting Officer*

JAMES E. ROGAN
*Director of the United States Patent and Trademark Office*